United States Patent [19]

Hübner et al.

[11] Patent Number: 4,895,803
[45] Date of Patent: Jan. 23, 1990

[54] METHOD FOR DECONTAMINATION OF MYCOPLASMA-INFECTED CELL CULTURES

[75] Inventors: Günter E. Hübner, Wuppertal; Helmut Brunner, Langenfeld; Hans-Joachim Zeiler, Velbert, all of Fed. Rep. of Germany

[73] Assignee: Bayer Aktiengesellschaft, Leverkusen, Fed. Rep. of Germany

[21] Appl. No.: 921,995

[22] Filed: Oct. 22, 1986

[30] Foreign Application Priority Data

Nov. 7, 1985 [DE] Fed. Rep. of Germany ....... 3539393
May 27, 1986 [DE] Fed. Rep. of Germany ....... 3617803

[51] Int. Cl.$^4$ ........................... C12N 5/00; C12N 5/02
[52] U.S. Cl. ............................. 435/240.1; 435/240.2; 435/240.3; 435/240.31
[58] Field of Search ............ 435/240.1, 240.2, 240.21, 435/240.22, 240.23, 240.25, 240.3, 240.31, 800; 544/37, 38, 58.6, 73, 102, 103, 104, 126, 127, 128, 349, 361, 363; 546/95, 123, 155, 156

[56] References Cited

U.S. PATENT DOCUMENTS 4,544,658 10/1985 Peterson et al. .................... 514/254
4,556,658 12/1985 Grohe et al. ........................ 514/254

OTHER PUBLICATIONS

McGarrity et al, "Methods of Prevention, Control and Elimination of Mycoplasma Infection"; in *Mycoplasma Infection of Cell Cultures*, McGarrity et al, editors, Plenum Press, N.Y., pp. 213, 235–241, 1978.

(List continued on next page.)

*Primary Examiner*—Charles F. Warren
*Assistant Examiner*—G. F. Knox
*Attorney, Agent, or Firm*—Sprung Horn Kramer & Woods

[57] ABSTRACT

A method for decontaminating cell cultures comprising contacting cell cultures with quinolone- and 1,8-naphthyridonecarboxylic acids of the formula (I)

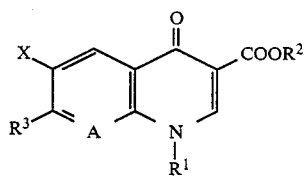

in which
$R^1$ represents methyl, ethyl, propyl, isopropyl, cyclopropyl, vinyl, 2-hydroxyethyl, 2-fluorethyl, methoxy, amino, methylamino, dimethylamino, ethylamino, phenyl, 4-fluorophenyl or 2,4-difluorophenyl, $R^2$ represents hydrogen, alkyl having 1 to 4 carbon atoms, or (5-methyl-2-oxo-1,3-dioxol-4-yl)-methyl,
$R^3$ represents methyl or a cyclic amino group such as

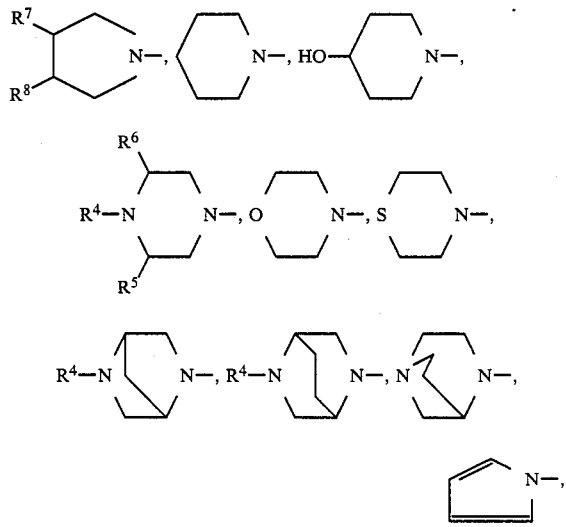

in which
$R^4$ represents hydrogen, alkyl having 1 to 4 carbon atoms, 2-hydroxyethyl, allyl, propargyl, 2-oxopropyl, 3-oxobutyl, phenacyl, formyl, $CFCl_2$—S—, $CFCl_2$—$SO_2$—, $CH_3O$—CO—S—, benzyl, 4-aminobenzyl or

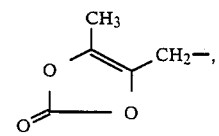

$R^5$ represents hydrogen or methyl,
$R^6$ represents hydrogen, alkyl having 1 to 4 carbon atoms, phenyl or benzyloxomethyl,
$R^7$ represents hydrogen, amino, methylamino, ethylamino, aminomethyl, methylaminomethyl, ethylaminomethyl, dimethylaminomethyl, hydroxyl, or hydroxymethyl,
$R^8$ represents hydrogen, methyl, ethyl or chlorine
X represents fluorine, chlorine or nitro and
A represents N or C-$R^9$, in which
$R^9$ represents hydrogen, halogen such as fluorine or chlorine, methyl or nitro, or can also, together with $R^1$, form a bridge of the structure —O—$CH_2$—CH—$CH_3$, —S—$CH_2$—CH—$CH_3$ or —$CH_2$—$CH_2$—CH—$CH_3$.

16 Claims, No Drawings

OTHER PUBLICATIONS

Journal Antimicrob. Chemother., Band 15, No. 6, Jun. 1985, pp. 787–789; fallon, R. J. et al, "In–Vitro Sensitiv. of Legionellas, menin., and Mycoplasmas to Cipro. and Enoxacin".

European Journal of Clinical Microbiology, Band 3, No. 4, Aug. 1984, pp. 344–346; G. L. Ridgway et al: "The Activ, of Ciproflox. and Other 4–Quin. Against Chloamydia Trach. and Mycop. in Vitro".

Antimicrobial Agents and Chemo., Band 23, No. 5, May 1983, pp. 641–648, *Amer. Soc. for Microbiology*, US; S. Nakamura et al.: "In Vitro Antibacterial Prop. of AT-2266 a New Pyridonecarb. Acid".

Antimicrobial Agents and Chemotherapy, Band 23, No. 3, Mar. 1983, pp. 509–511, *Amer. Soc. for Microbiology*, US; Y. Osada et al, "Antimycoplasmal Activity of Ofloxacin" (DL-8280).

Journal of Chrom., Band 339, No. 1, 1985, pp. 214–218, Elsevier Sci. Pub. B.V., Amsterdam, NL; G. Montay et al: "Improved High–Performance Liquid Chromatographic Determination of Pefloxacin and Its Metab. Norflox. in Human Plasma and Tissue".

European Journal of Clin. Micro., Band 2, No. 5, Oct. 1983, pp. 479–480; C. Simon et al, "In Vitro Acitivity of Norfloxacin Against Mycoplasma Hominis and Ureaplasam Urealyticum".

Experimental Cell Research, Band 152, 1984, pp. 565–570, Academic Press, Inc., J. Schmidt et al: "Elimination of Mycoplasmas From Cell Cultures and Establishment of Mycoplasma–Free Cell Lines".

Journal of Immunoglogical Methods, Band 109, No. 1, 1988, pp. 17–25, Elsevier Sci. Pub. B.V.; K. Schmitt et al: "A Safe and Efficient Method for Elimination of Cell Culture Mycoplasmas Using Ciproflox".

Perlman, "Use of Antibiotics in Cell Culture Media", Methods in Enzymology, vol. 58, 110–116, 1979.

METHOD FOR DECONTAMINATION OF MYCOPLASMA-INFECTED CELL CULTURES

BACKGROUND OF THE INVENTION

1. Field of the Invention

The invention relates to a method for decontamination of cell culture media by contacting cell culture media with quinolone and 1,8-naphthyridone-3-carboxylic acids.

2. Background Information

Cell cultures, in particular permanent cell lines, are frequently contaminated with mycoplasmas which may induce many uncontrollable changes in the cell cultures. In contrast to infections with bacteria and fungi, mycoplasma infection often remains unrecognised because even heavily contaminated cell cultures may show normal growth and the culture medium remains clear.

For many purposes in fundamental research (for example, genetic and physiological factors in the cells of a culture), in applied research (for example, lymphocytic cell fusion for obtaining monoclonal antibodies) and, above all, in the biotechnological utilization of cell cultures, for example, obtaining a product for administration to humans, it is necessary to work with mycoplasma-free cell cultures. Once a culture has become contaminated with mycoplasmas it is extremely difficult, if not impossible in many cases, to decontaminate this culture again, although decontamination has been achieved on occasion with various techniques. Thus, infected cell cultures have been subjected to hyperthermic treatment at 41° C. for 18 hours (L. Hayflick, *Nature*, 185, 783-784, 1960), or the cells have been treated with bromouracil or bromodeoxyuridine plus the fluorochrome Hoechst 33258 and UV light (M. Marcus et al., *Nature*, 285, 659-661, 1980; K. J. Fowler et al., *Exp. Cell Res.*, 149, 303-306, 1983) or they have been incubated with macrophages in the presence or absence of antibiotics (L. Schimmelpfeng et al., *Nature*, 285, 661-662, 1980), or they have been subjected to passage through the nude mouse (D. N. Howell et al., *Human Immunol.*, 5, 233-238, 1982). However, none of these methods is suitable for routine decontamination.

It has also been stated that treatment of mycoplasma-contaminated cell cultures and cell lines with the antibiotics tiamulin and minocycline results in mycoplasma-free cultures. However, in order to establish absolutely mycoplasma-free cultures, especially with valuable cell lines, it is necessary to carry out various steps of treatment, cloning of the cells and control studies (J. Schmidt & V. Erfle, *Exp. Cell Res.*, 152, 565-570, 1984).

SUMMARY OF THE INVENTION

It has now been found that quinolone- and 1,8-naphthyridone carboxylic acids of the formula (I)

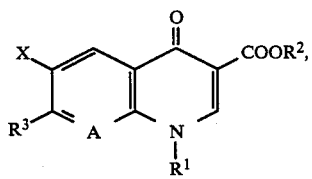

in which

R$^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl, R$^2$ represents hydrogen, alkyl having 1 to 4 carbon atoms, or (5-methyl-2-oxo-1,3-dioxol-4-yl)-methyl, R$^3$ represents methyl or a cyclic amino group such as

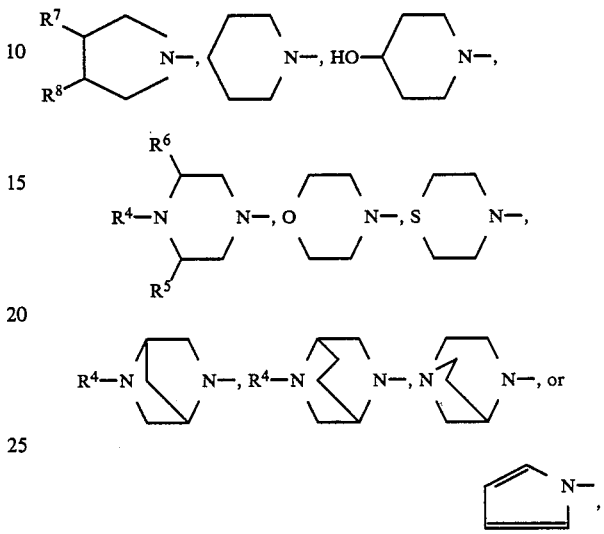

in which

R$^4$ represents hydrogen, alkyl having 1 to 4 carbon atoms, 2-hydroxyethyl, allyl, propargyl, 2-oxopropyl, 3-oxobutyl, phenacyl, formyl, CFCl$_2$—S—, CFCl$_2$—SO$_2$—, CH$_3$O—CO—S—, benzyl, 4-aminobenzyl of

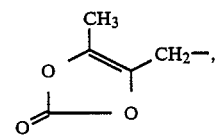

R$^5$ represents hydrogen or methyl,

R$^6$ represents hydrogen, alkyl having 1 to 4 carbon atoms, phenyl or benzyloxomethyl, R$^7$ represents hydrogen, amino, methylamino, ethylamino, aminomethyl, methylaminomethyl, ethylaminomethyl, dimethylaminomethyl, hydroxyl or hydroxymethyl, R$^8$ represents hydrogen, methyl, ethyl or chlorine, X represents fluorine, chlorine or nitro and A represents N or C—R$^9$, in which R$^9$ represents hydrogen, halogen such as fluorine or chlorine, methyl or nitro, or can also, together with R$^1$, form a bridge of the structure O—CH$_2$—CH—CH$_3$, —S—CH$_2$—CH—CH$_3$ or

—CH$_2$—CH$_2$—CH—CH$_3$ preferably in concentrations between 1 and 1000 μg/ml of cell culture, particularly preferably 20 to 100 μg/ml of cell culture, very particularly preferably 50 μg/ml of cell culture, on treatment of cell cultures, which are optionally incubated at the same time with tiamulin and minocycline as well, result in decontamination of particularly resistant mycoplasma infections as are frequently present in cultures of adherent cells, in which treatment with tiamulin and minocycline alone does not result in success. The process requires a treatment time of only seven days to achieve a permanent decontamination of the culture. Various other steps such as, for example, cloning of the cells can be entirely dispensed with.

DETAILED DESCRIPTION OF THE INVENTION

It is expedient to use 1 to 1000 μg of the active compound per ml of cell culture for the decontamination.

It is particularly preferable to use for the purpose according to the invention ciprofloxacin, norfloxacin, pefloxacin, amifloxacin, pirfloxacin, piroxacin, ofloxacin and enoxacin.

1-Cyclopropyl-6-fluoro-1,4-dihydro-4-oxo-7-piperazinoquinoline-3-carboxylic acids of the formula II

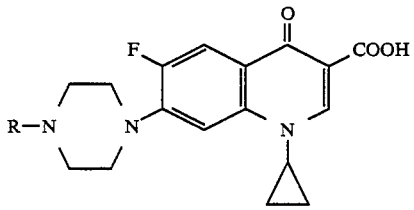

in which
R denotes hydrogen, methyl, ethyl or β-hydroxyethyl, their pharmaceutically utilizable acid addition salts and hydrates,
are preferably used according to the invention.

The invention also very particularly relates to the use of 1-cyclopropyl-6-fluoro-1,4-dihydro-4-oxo-7-piperazinoquinoline-3-carboxylic acid and 1-cyclopropyl-6-fluoro-1,4-dihydro-4-oxo-7-(4-ethylpiperazino)-quinoline-3-carboxylic acid, as well as the compounds of the examples, for decontamination of mycoplasmas from cell cultures in such a manner that the decontamination with 1-cyclopropyl-6-fluoro-1,4-dihydro-4-oxo-7-piperazinoquinoline-3-carboxylic acid is carried out in parallel with a treatment of the cell cultures with 6-ethenyldecahydro-5-hydroxy-4,6,9,10-tetramethyl-1-oxo-3a,9-propano-3aH-cyclopentacycloocten-8-yl [(2-(diethylamino)ethyl)-thio]-acetate=tiamulin and/or 4,7-bis(dimethylamino)-1,4,4a,5,5a,6,11,12a-octahydro-3,10,12,12a-tetrahydroxy-1,11-dioxo-2-naphthacenecarboxamide=minocycline. This entails the use of 1 to 1000 μg of tiamulin and/or minocycline per ml of cell culture. The treatment is effected in such a manner that the active compound 1-cyclopropyl-6-fluoro-1,4-dihydro-4-oxo-7-piperazinoquinoline-3-carboxylic acid or 1-cyclopropyl-6-fluoro-1,4-dihydro-4-oxo-7-(4-ethylpiperazino)-quinoline-3-carboxylic acid is allowed to act on the cell culture for 7 to 14 days, and where appropriate combined with the active compounds tiamulin and/or minocycline.

The invention furthermore relates to the use of quinoline- and 1,8-naphthyridone-3-carboxylic acids of the formulae (I) and (II) for the preparation of compositions for decontamination of mycoplasma-infected cell cultures and, in particular, to the use of 1-cyclopropyl-6-fluoro-1,4-dihydro-4-oxo-7-piperazinoquinoline-3-carboxylic acid, where appropriate in combination with tiamulin and/or minocycline, for the preparation of compositions of this type.

Finally, the invention also relates to cell culture media containing quinoline- and 1,8-naphthyridone-3-carboxylic acids of the formulae (I) and (II) and to cell cultures containing quinoline- and naphthyridone-3-carboxylic acids of the formulae (I) and (II) and optionally tiamulin and/or minocycline.

It is appropriate and expedient when a mycoplasma infection has been detected in cell cultures, especially in valuable cell lines, to carry out a fresh inoculation of these cells in a suitable culture medium at a density of, for example, $10^3-10^6$ cells/ml in a suitable culture vessel such as, for example, a cell culture bottle made of plastic material. It is then possible to add to these freshly inoculated cells a previously prepared solution of, for example, ciprofloxacin, and optionally a solution of tiamulin and/or minocycline. The antibiotic can be, for example, dissolved in the cell culture medium and added to the cell culture in the necessary volume as required; thus, for example, it is useful to pipette about 100-500 μl of antibiotics solution into about 5-20 ml of cell culture. Once the cells and antibiotics have been inoculated the cells grow in the days which follow; it is then possible for ciprofloxacin, and tiamulin and/or minocycline where appropriate, to exert its antiinfective effect on the mycoplasmas during this time. Once the culture has grown densely (stationary phase of growth) it is advisable to harvest the cells using a technique known to the expert and to carry out another fresh inoculation, at a lower cell density, into a new culture vessel; fresh culture medium ought to be used for this purpose and, if needed, ciprofloxacin solution, and tiamulin and/or minocycline solution where appropriate, should be added.

EXAMPLES

EXAMPLE 1

Suspended or adherent cells of various cell lines (for example U 266 human myeloma cells and L 929 mouse fibroblasts) which were contaminated with mycoplasmas of unidentified specificity were inoculated at a concentration of $10^5$/ml and a volume of 10–15 ml into 75 cm$^3$ cell culture bottles. The culture medium used was RPMI 1640 containing 10% of fetal calf serum (FCS), L-glutamine (2 mM), hepes, buffer (4 mM) and 2-mercaptoethanol (50 μM). After 3–4 days in each case the cultures were in the stationary phase, in which they were than harvested (in the case of adherent cells by use of trypsin/EDTA [0.25%/0.02%]). The cells were then inoculated again at $10^5$/ml in fresh medium.

To treat the mycoplasma contamination, the following were added to the cultures: (a) tiamulin (10 μg/ml, for 4 days), and then minocycline (5 μg/ml, for 3 days); (b) ciprofloxacin (50 μg/ml, for 7 days); (c) tiamulin and minocycline as under (a) plus ciprofloxacin as under (b). At the end of each exposure time the antibiotics were washed-out with medium and the cells were subjected to further passages. Before the treatment and at various times after the treatment, 0.1 ml of cell culture was smeared onto Hayflick's agar for the detection of mycoplasma (L. Hayflick, *Texas Reports Biol. Med.*, 23, Suppl. 1, 285–300, 1965) and incubated anaerobically at 37° C. for at least one week.

The agar medium used (5 ml per Petri dish) had the following composition: PPLO agar (from Difco Co.; 70 parts), horse serum (20 parts), yeast extract (from Flow Labs.; 25% strength; 10 parts), glucose (50% strength, 2 parts), benzylpenicillin (100000 U/ml; 1 part) and thallium-I acetate (2% strength; 2.5 parts). The development of colonies with a typical "fried egg shape" on the agar signifies contamination of the cell culture with mycoplasmas. Table 1 shows results from treated L 929 cell cultures.

Table 1

Mycoplasma contamination in L 929 cell cultures at various times after treatment for 7 days with tiamulin/-minocycline (T/M), ciprofloxacin (C), tiamulin-ciprofloxacin/minocycline-ciprofloxacin (T-C/M-C) or without treatment (φ); + = mycoplasma contamination, − = no mycoplasma contamination

| Days | 0 | 4 | 7 | 14 | 21 | 31 | 36 |
|---|---|---|---|---|---|---|---|
| T/M | − | + | + | + | + | + | + |
| C | − | − | − | + | + | + | + |
| T-C/M-C | − | − | − | − | − | − | − |
| φ | + | + | + | + | + | + | + |

Whereas no mycoplasmas were detectable in any of the three treatment groups immediately after the treatment, mycoplasmas were found again 4 days after discontinuation of the tiamulin/minocycline treatment, while no mycoplasmas were detectable for 7 days after ciprofloxacin treatment. In contrast to this, over a month after the combination treatment with tiamulin-ciprofloxacin/minocycline-ciprofloxacin mycoplasmas were still undetectable, so that these cells have to be regarded as decontaminated.

EXAMPLE 2

The active compound used was 1-cyclopropyl-6-fluoro-1,4-dihydro-4-oxo-7-(4-ethylpiperazino)-quinoline-3-carboxylic acid which is identified by the capital letter A below.

Suspended or adherent cells of various cell lines (for example U 266 human myeloma cells and L 929 fibroblasts) which were contaminated with mycoplasmas of unidentified specificity were inoculated at a concentration of $10^5$ cells/ml and a volume of 10–15 ml into 75 cm$^3$ cell culture bottles. The culture medium used was RPMI 1640 containing 10% of fetal calf serum (FCS), L-glutamine (2 mM), and hepes buffer (4 mM). After 3–4 days in each case the cultures were in the stationary phase, in which they were then harvested (in the case of adherent cells by the use of trypsin/EDTA [0.25%/0.02%]). The cells were then inoculated again at $10^5$ cells/ml in fresh medium.

To treat the mycoplasma contamination, the following were added to the cultures: (a) A (50 μg/ml, for 7 days); (b) A (10 μg/ml, for 4 days) plus tiamulin (10 μg/ml, for 4 days and then A (10 μg/ml, for 3 days) plus minocycline (5 μg/ml, for 3 days). At the end of each exposure time the antibiotics were washed-out with medium and the cells were subjected to further passages. Before the treatment and at various times after the treatment 0.1 ml of cell culture was smeared onto Hayflick's agar for the detection of mycoplasmas (L. Hayflick, *Texas Reports Biol. Med.*, 23, Suppl. 1, 285–300, 1965) and incubated anaerobically at 37° C. for at least one week.

The agar medium used (5 ml per Petri dish) had the following composition: PPLO agar (from Difco Co.; 70 parts), horse serum (20 parts), yeast extract (from Flow Labs.; 25% strength; 10 parts), glucose (50% strength, 2 parts), benzylpenicillin (100000 U/ml; 1 part) and thallium-I acetate (2% strength; 2.5 parts). The development of colonies with typical "fried egg shape" on the agar signifies contamination of the cell culture with mycoplasmas. Table 2 shows results of treated U 266 cell cultures.

Table 2

Mycoplasma contamination in U 266 cell cultures at various times after treatment for 7 days with 50 μg/ml A or 10 μg/ml A together with 10 μg/ml tiamulin for 4 days and then together with 5 μg/ml minocycline for 3 days (T-A/M-A) or without treatment (φ); + = mycoplasma contamination, − = no mycoplasma contamination

| Day | 0 | 21 | 28 | 35 |
|---|---|---|---|---|
| A | − | − | − | − |
| T-A/M-A | − | − | − | − |
| φ | + | + | + | + |

In contrast to the untreated control no mycoplasmas were detectable in either treatment group over one month after the end of the treatment. Hence these cells must be regarded as decontaminated.

EXAMPLE 3

The culture and test conditions in this example are the same as in the Example 2. In this case, merely quinolones were employed in U 266 cell cultures without use being made of tiamulin or minocycline.

8-Chloro-1-cyclopropyl-6-fluoro-1,4-dihydro-4-oxo-7-(3-methyl-1-piperazinyl)-3-quinolinecarboxylic acid = B, 8-chloro-1-cyclopropyl-6-fluoro-1,4-dihydro-4-oxo-7-(1-piperazinyl)-3-quinolinecarboxylic acid = D and 8-chloro-1-cyclopropyl-6-fluoro-7-methyl-1,4-dihydro-5-oxo-3-quinolinecarboxylic acid = E were used.

Table 3

Mycoplasma contamination in U 266 cell cultures at various times after treatment for 7 days with 10 μg/ml of each of substances B (B), or D (D), or E (E) dissolved in ethanol plus sonication (ethanol concentration in culture 0.25%), or without treatment φ); + = mycoplasma contamination, − = no mycoplasma contamination

| Days | 0 | 21 | 28 | 35 |
|---|---|---|---|---|
| B | − | − | − | − |
| D | − | − | − | − |
| E | − | − | − | − |
| φ | + | + | + | + |

In contrast to the untreated control, all the treatments were successful so that no mycoplasma contamination was detectable over one month after the end of the treatment. These cultures must therefore be regarded as decontaminated. Finally, it ought also to be pointed out that the substances D and E exerted slight toxic effects on the cultures, that is to say proliferation of the cells was inhibited during the treatment, but there was no evident reduction in the ability of the cells to proliferate after the end of the treatment.

It will be appreciated that the instant specification and claims are set forth by way of illustration and not limitation, and that various modifications and changes may be made without departing from the spirit and scope of the present invention.

We claim:

1. A method for decontaminating mycoplasma-infected cell cultures comprising contacting said cell cultures with an effective decontaminating amount of a active compound comprising quinolone- or 1,8-naphtyridonecarboxylic acid of the formula (I)

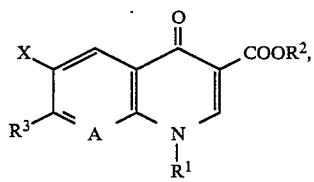

in which
$R^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl,
$R^2$ represents hydrogen, alkyl having 1 to 4 carbon atoms, or (5-methyl-2-oxo-1,3-dioxol-4-yl)-methyl,
$R^3$ represents methyl or a cyclic amino group selected from the group consisting of

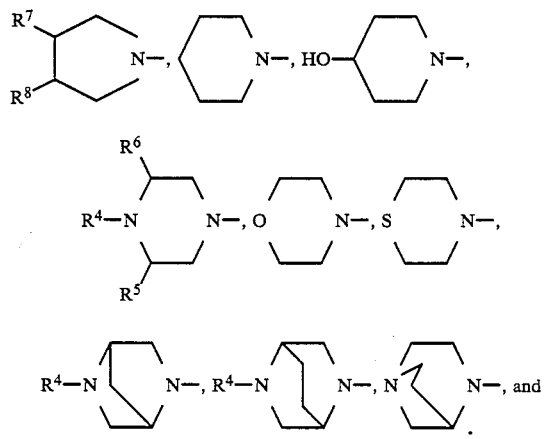

in which
$R^4$ represents hydrogen, alkyl having 1 to 4 carbon atoms, 2-hydroxyethyl, allyl, propargyl, 2-oxopropyl, 3-oxobutyl, phenacyl, formyl, $CFCl_2-S-$, $CFCl_2-SO_2-$, $CH_3O-CO-S-$, benzyl, 4-aminobenzyl or

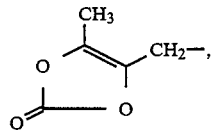

$R^5$ represents hydrogen or methyl,
$R^6$ represents hydrogen, alkyl having 1 to 4 carbon atoms, phenyl or benzyloxymethyl, $R^7$ represents hydrogen, amino, methylamino, ethylamino, aminomethyl, methylaminomethyl, ethylaminomethyl, dimethylaminomethyl, hydroxyl or hydroxymethyl,
$R^8$ represents hydrogen, methyl, ethyl or chlorine,
X represents fluorine, chlorine or nitro and
A represents N or $C-R^9$, in which
$R^9$ represents hydrogen, halogen, methyl or nitro, or $R^9$ together with $R^1$ forms a bridge of a structure selected from the group consisting of $-O-CH_2-CH-CH_3$, $-S-CH_2-CH-CH_3$ and $-CH_2-CH_2-CH-CH_3$, said method not requiring cloning to achieve permanent decontamination.

2. A method according to claim 1, wherein for $R^9$, the halogen is selected from the group consisting of fluorine and chlorine.

3. A method according to claim 1, wherein 1 to 1000 µg of active compound is used per ml of cell culture.

4. A method according to claim 1, wherein 20 to 100 µg of active compound is used per ml of cell culture.

5. A method according to claim 1, further comprising treating said cell cultures with tiamulin and/or minocycline.

6. A method according to claim 5, wherein 1 to 1000 µg of active compound and 1 to 1000 µg of tiamulin and/or minocycline per ml of cell culture are employed.

7. A method according to claim 1, wherein the active compound is allowed to act on the cell culture for 7 to 14 days.

8. A method according to claim 5, wherein the active compound and the tiamulin and/or minocycline are allowed to act on the cell culture for 7 to 14 days.

9. A method according to claim 1, wherein the active compound is selected from the group consisting of ciprofloxacin, norfloxacin, pefloxacin, amifloxacin, pirfloxacin, piroxacin, ofloxacin and enoxacin.

10. A method for decontaminating mycoplasma-infected cell cultures comprising contacting said cell cultures with an effective decontaminating amount of an active compound comprising a 1-cyclopropyl-6-fluoro-1,4-dihydro-4-oxo-7-piperazino-quinoline-3-carboxylic acid of the formula

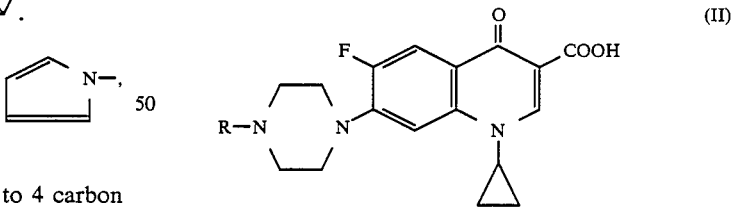

in which
R denotes hydrogen, methyl, ethyl or hydroxyethyl, and of their pharmaceutically utilizable acid addition salts and hydrates, said method not requiring cloning to achieve permament decontamination.

11. A method according to claim 10, wherein 1 to 1000 µg of active compound is used per ml of cell culture.

12. A method according to claim 10, further comprising treating said cell cultures with tiamulin and/or minocycline.

13. A method according to claim 12, wherein 1 to 1000 µg of the active compound and 1 to 1000 µg of tiamulin and/or minocycline per ml of cell culture are employed.

14. A method according to claim 10, wherein the active compound is allowed to act on the cell culture for 7 to 14 days.

15. A method according to claim 12 wherein the active compound and the tiamulin and/or minocycline are allowed to act on the cell culture for 7 to 14 days.

16. A method according to claim 10, wherein the active compound is selected from the group consisting of 1-cyclopropyl-6-fluoro-1,4-dihydro-4-oxo-7-piperazinoquinoline-3-carboxylic acid and 1-cyclopropyl-6-fluoro-1,4-dihydro-4-oxo-7-(4-ethyl-piperazine)-quinoline-3-carboxylic acid.

* * * * *